United States Patent [19]

Narayanan

[11] Patent Number: 5,698,211
[45] Date of Patent: *Dec. 16, 1997

[54] STABILIZED AGCHEMICAL CONCENTRATE AND USE THEREOF

[75] Inventor: Kolazi S. Narayanan, Palisades Park, N.J.

[73] Assignee: ISP Investments Inc., Wilmington, Del.

[*] Notice: The term of this patent shall not extend beyond the expiration date of Pat. No. 5,425,955.

[21] Appl. No.: 142,627

[22] Filed: Oct. 25, 1993

Related U.S. Application Data

[63] Continuation-in-part of Ser. No. 975,811, Nov. 13, 1992, and Ser. No. 17,093, Feb. 12, 1993, Pat. No. 5,425,955.

[51] Int. Cl.$^6$ .......................... A01N 25/04; A01N 25/14; A01N 25/30; A01N 25/24
[52] U.S. Cl. .......................... 424/409; 424/405; 424/407; 71/64.02; 71/DIG. 1; 523/122; 504/113
[58] Field of Search ...................... 514/772.5, 937, 514/938; 424/405, 407, 409; 523/122; 504/113; 71/64.02

[56] References Cited

U.S. PATENT DOCUMENTS 5,231,070  7/1993  Narayaman et al. ............... 504/113

OTHER PUBLICATIONS

Kirk–Othmer Encyclopedia of Chemical Technology, 3rd ed, vol. 8, p. 910.

*Primary Examiner*—Edward J. Webman
*Attorney, Agent, or Firm*—Marilyn J. Maue; Walter Katz; Joshua J. Ward

[57] ABSTRACT

The present invention relates to the stabilization of an agricultural chemical concentrate in aqueous solution and the stabilized concentrate which comprises:

(a) between about 0.1 and about 20 wt. % of a stabilizer composition comprising:

(1) between about 10 and about 90 wt. % of a water-insoluble, non-crosslinked, film forming polymer, and (2) a polymer solubilizing amount of an aromatic petroleum distillate or an oxygen-containing solvent of an N-alkyl pyrrolidone, a $C_3$ to $C_8$ alkanol, a dibasic acid lower alkyl ester, an ether having a boiling point above 150° C. or mixtures thereof and (b) between about 80 and about 99.9 wt. % concentrate containing a water-insoluble active agricultural chemical, a solvent for said agricultural chemical and a surfactant for said concentrate. The invention also relates to the use of said stabilized concentrate.

14 Claims, No Drawings

STABILIZED AGCHEMICAL CONCENTRATE AND USE THEREOF

This application is a continuation-in-part of Ser. No. 07/975,811, filed Nov. 13, 1992 and U.S. Ser. No. 08/017,093, filed Feb. 12, 1993, now U.S. Pat. No. 5,425,955 in the name of Kolazi S. Narayanan and entitled "COMPOSITIONS OF INSOLUBLE FILM-FORMING POLYMERS AND USES THEREFOR"

In one aspect the invention relates to an emulsion stabilizer for active chemical concentrates, and, in another aspect, to the stabilization of a water insoluble agriculturally active concentrate to provide a stable emulsion, which emulsion can be dried to a free-flowing powder or can be diluted with water to form a film forming, non-crystalizing, sprayable liquid containing an effective amount of agrichemical.

BACKGROUND OF THE INVENTION

Aqueous emulsions are desirable delivery systems for many water insoluble, chemically active compounds since such emulsions provide a cost effective, carrier system which accommodates high concentrations of the active component in a uniformly distributed, aqueous, single-phase medium, which is convenient to apply by spraying. Of particular interest are aqueous emulsions of water insoluble agrichemicals which are generally prepared by combining the active component with an inert emulsifiable carrier or matrix containing a surfactant and a solvent to form an emulsion concentrate which can be subsequently diluted with water to a desired active concentration as a sprayable product. Although many of these emulsions are environmentally safe and convenient to apply, the agriculturally active component tends to precipitate in the form of inactivated crystals within a short time after dilution; thus preventing uniform distribution of the active component and markedly reducing the efficacy of the treatment. The easy removal of crystals by rain water is also a serious consideration since ground deposits of the agrichemical prevents its use for the function intended and tends to build-up on the soil. This is particularly troublesome in the few cases where the active chemical is harmful to humans and the environment.

Accordingly, it is an object of the invention to provide an emulsion stabilizer which, when combined with the agriculturally active chemical concentrate, minimizes or delays crystal formation for significantly extended periods.

Another object of this invention is to provide an agriculturally active chemical concentrate composition having film forming properties which retards removal of the active ingredient from the treating side under climatic conditions.

Another object of the invention is to provide a method for the formation of an emulsion stabilized agrichemical concentrate.

Yet another object is to provide an environmentally safe agrichemical concentrate which is more economically packaged and stored for delivery or use.

These and other objects of the invention will become apparent to those skilled in the art from the following description and disclosure.

THE INVENTION

In accordance with this invention, there is provided a stabilized agrichemical concentrate which comprises between about 0.1 and about 20 wt. % of a water insoluble, non-crosslinked, film forming N-vinyl $C_4$ to $C_7$ lactam polymer optionally substituted on a ring carbon atom with lower alkyl or an alkyl vinyl ether/organic acid ester copolymer, dissolved in a solubilizing liquid (species defined hereinafter) and between about 80 and about 99.9 wt. % of an agrichemical, solvent and surfactant mixture. More particularly, the stabilized agrichemical concentrate of this invention comprises (a) between about 0.1 and about 20 wt. % of a solubilizing composition containing (1) between about 10 and about 90 wt. % of a water insoluble, non-crosslinked polymer selected from the group of a N-vinyl lactam/$C_4$ to $C_{20}$ alpha-olefin copolymer in a weight ratio of from about 90:10 to about 20:80, an N-vinyl lactam/vinyl acetate copolymer, styrene/N-vinyl lactam copolymer, polyvinylpyrrolidone having a K-value of between about 50 and about 90, polyvinyl caprolactam of 20 to 100K value and a $C_1$ to $C_{12}$ alkyl vinyl ether/acid ester copolymer wherein said lactam moiety is a cyclic amide having 4 to 7 carbon atoms in the ring and wherein said ring carbon atoms can be substituted with a lower alkyl ($C_1$ to $C_4$) group and (2) a polymer solubilizing amount of a petroleum distillate or an oxygen-containing aprotic solvent selected from the group of an N—$C_8$ to $C_{16}$ alkylpyrrolidone, a $C_3$ to $C_{12}$ alkanol, a dibasic acid ester and a non-volatile ether having a boiling point above 150° C. and (b) between about 80 and about 99.9 wt. % of a concentrate containing a water insoluble, active agricultural chemical, a solvent for said agrichemical and a surfactant mixture for said concentrate. The preferred N-vinyl lactams are N-vinyl $C_4$ to $C_6$ lactams optionally substituted on a ring carbon atom with lower alkyl. The preferred polymer solvents are water insoluble such as the N—$C_8$ to $C_{16}$ alkyl pyrrolidones, petroleum distillates, vegetable oils, $C_8$ to $C_{12}$ alkanols, etc.

The stabilizing composition is provided in a form of a solution containing between about 10 and about 90 wt. % of the polymer, and is preferably, a copolymer of an N-vinylpyrrolidone and a $C_{10}$ to $C_{18}$ alpha-olefin in a weight proportion of from about 70:30 to about 30:70 and most preferably, 50:50 N-vinylpyrrolidone/1-hexadecene copolymer (Ganex® 516, supplied by ISP).

Suitable polymer solvents for the stabilizing agent are employed in the above solubilizing solution in a concentration of between about 10 to 90 wt. %, preferably 70 to 50 wt. % and are selected on a case by case basis and are preferably those having surfactant properties. Suitable polymer solvents include N-methylpyrrolidone; N-octylpyrrolidone; N-dodecyl-pyrrolidone; mono- and poly-hydric alcohols such as isopropyl alcohol, n-propanol, butanol, hexanol, octanol, glycerol, ethylene glycol; non-volatile ethers such as glycol ethers, dibasic acid esters such as diethyl adipate, diethyl glutarate, diethyl succinate; a petroleum distillate boiling between about 70° and about 250° C., e.g. an aliphatic petroleum distillate fraction boiling between 70°–150° C., an aromatic petroleum distillate fraction boiling between 140°–250° C. such as Exxon aromatic 150 and 200 and Shell's Sol solvents and mixtures of the above polymer solvents. Of these, the water insoluble N-alkyl pyrrolidones are most effective.

The polymers useful in this invention include the homo- and co-polymers of N-vinylpyrrolidone and N-vinyl caprolactam which are optionally substituted on their respective rings with lower alkyl and which may have as their comonomer species vinyl acetate or an α-olefin such as 1-butene, 1-hexene, 1-octene, 1-decene, 1-dodecene, 1-hexadecene, 1-octadecene, and the like. Other suitable polymers include vinyl ether/ester copolymers such as octyl vinyl ether/terephthalic acid ester, hexyl vinyl ether/fumaric acid ester; methyl vinyl ether/vinyl acetate copolymers; $C_1$ to $C_4$ alkyl vinyl ether/maleic ester copolymers; block copolymers of styrene/N-vinyl pyrrolidone and mixtures of such polymers.

The present polymer stabilizing solution is prepared under ambient conditions of temperature and pressure with mixing until a homogeneous product solution is obtained, usually within a period of from about 5 minutes to about 24 hours. This stabilizer solution is suitably combined with an active chemical concentrate prior to its dilution for use.

As indicated above, conventional agrichemical concentrates are employed and stabilized in the compositions of this invention. For example, agrichemical concentrate comprises an effective amount of a water insoluble active chemical, between about 10 and about 80 wt. % of a suitable solvent for the active chemical and between about 1 and about 30 wt. % of a surfactant mixture containing both anionic and non-ionic surfactants or a mixture of non-ionic surfactants.

Suitable solvents for the chemically active component include N-octylpyrrolidone, N-methylpyrrolidone, aromatic petroleum oil distillates, $C_1$ to $C_4$ alkyl diesters of carboxylic acids, such as dialkyl adipate, dialkyl glutarate, dialkyl succinate, vegetable oils and the like.

The agriculturally active chemical in the concentrate is usually employed in a concentration of from about 5 to about 50 wt. %, most desireably from about 15 to about 25 wt. % of the concentrate. The active chemical concentrate may contain a small, dispersing amount of water, usually less than 30 wt. %. However, for use on a plant or plant site, the concentrate is diluted with water to a desired concentration so as to form an aqueous dispersion of at least 85 wt. % water, preferably 90 to 99.5 wt. % water. It is at this final dilution stage that problems develop when the stabilizer is omitted from the concentrate composition.

The surfactant mixture employed in the concentrate has a hydrophilic-hydrophobic balance (HLB) of from about 3 to about 20, preferably from about 7 to about 15, and most preferably from 8–12. The surfactants employed to provide the desired HLB mixture include non-ionics such as ethylene oxide-propylene oxide block polymers, ethoxylated alkyl phenols, linear aliphatic and aromatic polyesters, polyethoxylated alcohols, linear aliphatic ethoxylates, polyethoxylated castor oil, polyethoxylated carboxylates, alkoxylated glyceryl esters, organo silicones, polyethoxylated alkylamines and the like and anionic surfactants include phosphate esters and their salts, alkyl sulfonamides, salts of sulfated nonylphenoxypoly(ethyleneoxy) ethanol, salts of alkylbenzene sulfonates, salts of alkylnaphthalene sulfonate, sulfonated aliphatic polyesters and their salts and other aliphatic sulfonated surfactants. Also suitable are complex phosphate esters of nonionic surfactants of the ethylene oxide type which are mixtures of diesters of phosphoric acid (see, for example, McCutcheon's, Emulsifiers and Deteroents (1989), published by McCutcheon's Division of M. C. Publishing Co., Glen Rock, N.J.) Some specific examples of such anionics include sodium dodecyl sulfate (SDS), sodium dodecyl benzene sulfonate (LAS), ethoxylated nonyl phenol phosphates (RE 610), etc.

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or domestic uses for controlling insects and pests. Particularly, such chemicals would normally take the form of water-immiscible or oily liquids and/or solids which are substantially insoluble in water. By the term "substantially insoluble" or "water insoluble", it is meant that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithio-phosphates. (See Agricultural Chemicals, Book I, Insecticides, 1989 Revision by W. T. Thomson, Thomson Publications.) typical of the insecticides are:

Cyclo compounds:
(s)-α-cyano-M-phenoxybenzyl (1R, 3R)-3-(2,2-dibromovinyl) 2,2-dimethyl cyclopropane-carboxylate (DELTAMETHRIN);
6,7,8,9,10,10-hexachloro-1,5,5a,6,9,9a-hexahydro-6,9-methano-2,4,3-benzodioxathiepin-3-oxide Carbamates:
2-isopropyl phenyl-N-methyl carbamate;
2-(1,3-dioxolan-2-yl)phenylmethyl carbamate
2,3-isopropylidine dioxyphenyl methyl carbamate Animal & Plant Derivatives
chlorinated hydrocarbons derived from Southern pine
naturally occuring lactone glycoside Synthetic Pyrethroids:
α-cyano-3-phenoxybenzyl cis, trans 3-(2,2-dichlorovinyl)-2,2-dimethyl cyclopropane carboxylate;
cyano (3-phenoxyphenyl) methyl-4-(difluoromethoxy)-1-methylethyl)benzene acetate;

Phenoxy Compounds and Non-Phosphate:
2,2-bis(p-methoxy phenyl)-1,1,1,tri-chloroethane;
1,3,5,tri-n-propyl-1,3,5-triazine-2,4,6 (1H,3H,5H) trione;
ethyl (2E, 4E)-3,7,11-trimethyl-2,4-dodeca dienoate;
1-decycloxy 4-[(7-oxa-oct-4-ynyl)]-oxybenzene;

Organic Phosphates:
dimethyl phosphate ester of 3-hydroxy-N,N-dimethyl-cis-crotonamide;
2-chloro-1-(2,4-dichloro phenyl) vinyl diethylphosphate;
4-(methyl thio) phenyl dipropyl phosphate;

Thiophosphates:
O,O-diethyl-O-4-nitrophenyl phosphorothioate;
O,O-diethyl-O-(2,isopropyl-6-methyl-5-pyrimidinyl) phosphorothioate;
2-diethylamino-6-methyl pyrimidine-4-yl dimethyl phosphorothioate;

Dithiophosphates:
O,O-dimethyl phosphorodithioate ester of diethylmercapto succinate;
O-ethyl-S-phenyl ethyl phosphorodithioate.

Typical herbicides include phenoxy compounds, benzoic, acetic, and phthalic acids, aniline derivatives, nitriles, amides, acetamides, anilides, carbamates, thio-carbamates, and heterocyclic nitrogen derivatives, e.g., triazines, pyridines, pyridazones, picolinic acid, and urea derivates and phosphates. (See Agricultural Chemicals, Book II, Herbicides, 1986–87 Edition, W. T. Thomson, Thomson Publications, Fresno, Calif. 93791.) Exemplary of the above compounds are:

Phenoxy Compounds:
2,4-dichlorophenoxy acetic acid 2,4,5-trichloro phenoxy-acetic acid;

4-(2,4-dichlorophenoxy) butyric acid;
S-ethyl 2 methyl-4-chlorophenoxythioacetate;
2-methyl-4-chloro-phenoxy acetic acid;
methyl 5-(2,4-dichloro-phenoxy-2-nitrobenzoate;
Benzoic and Acetic Acids of Phthalic Compounds:
3,6-dichloro-o-anisic acid 4-chloro-2-oxo benzothiazolin-3-yl acetic acid;
N-1-Naphthyl-phthalamic acid;
Nitriles and Aniline Derivatives:
3-5-dibromo-4-hydroxybenzo-nitrile;
α,α,α,trifluoro-2,6-dinitro-N,N-dipropyl-p-tolinidine;
N-(1-ethylpropyl)-2,6-dinitro-3,4-xylidine;
Amides, Acetamides, Anilides:
N,N-diethyl-2-(1-naphthalenyl oxy)-propionamide;
2,6-dimethyl-N-2' methoxy-ethyl-chloro-acetanilide;
3',4'-dichloro-propionanilide;
α-chloracetic-N-(3,5,5-trimethyl-cyclohexen-1-yl)-N-isopropylamide;
4-benzyl-N-isopropyl trimethyl acetamide;
Thiocarbamates:
S-Ethyl dipropyl thiocarbamate;
Urea Derivatives:
3-(5-tert-butyl-3-isoxazoyl)-1,1-dimethyl urea;
N-(2,6-trifluoro-benzoyl)-N'-[2,5-dichloro-4-(1,1,2,3,3,3-hexafluoropropyloxy)phenyl] urea;
Pyrrolidone Derivatives:
1-(m-trifluoro methyl phenyl)-3-chloro-4-chloromethyl-2-pyrrolidone;
Amino Acid Derivatives:
methyl N-benzoyl-N-(3-chloro-4-fluorophenyl)-DL alarinate;
N-chloroacetyl-N-(2,6-diethylphenyl)-glycine ethyl ester;
Carbamates:
Isopropyl-m-chlorocarbanilate;
3-Ethoxy (carbonyl aminophenyl)-N-phenyl carbamate;
Heterocyclics:
4-amino-3,5-dichloro-6-fluoro-2-pyridyloxy acetic acid;
4-(1,2-Dimethyl-N-propyl amino)-2-ethyl amino-6-methyl thio-S-triazine;
2-[4,5-dihydro 4-methyl-4-(1-methylethyl)-5-oxo-1 H-imidazoyl-2yl-3-byridinecarboxylic acid;
2-[3,5-dichlorophenyl)-2-(2,2,2-trichloroethyl) oxinane;
Butyl-9-hydro-fluorene-(9)-carboxylate;
2-[1-(ethoxy imino) butyl]-3-hydroxy-5-(2H-tetra hydro thiopyran-3-yl)-2-cyclohexene-ione;
2-(2 chlorophenyl) methyl-4,4-dimethyl-3-iso oxazolidinone;
Phosphates:
O-ethyl-O-(3-methyl-6-nitro phenyl) N-sec-butyl phosphoro thio amidate.

Typical fungicides include (See *Agricultural Chemicals*, Book IV, *Fungicides*, 1989 Revision, W. T. Thomson, Thomson Publications, Fresno, Calif. 93791):
Organic Compounds:
2,5-dimethyl-N-Cyclohexyl-N-methoxy-3-furan carboxamide;
N-(4-tert-butylbenzyl)-4-chloro-3-ethyl-1-methylpyrazole-5-carboxamide (TEBUFENPYRAD);
5-Ethyoxy-3-trichloromethyl-1,2,4-thiadiazole;
3-(2-methyl piperidino) propyl 3,4-dichlorobenzoate;
N,N'-(1,4-piperazinediyl bis (2,2,2-trichloro) ethylidene) bis formamide;
Tetramethyl thiuram disulfide;
O-Ethyl-S,S,diphenyl-dithiophosphate;
5,10-dihydro-5,10-dioxo naphtho (2,3,9)-p-dithiin-2,3-dicarbonitrile;
2-(Thiocyano methyl thio) benzothiazole;
α-2-(4-chlorophenyl) ethyl]-α-(1,1-dimethyl ethyl)-1H-1,2,4-triazole-1-ethanol;
Morpholines:
N-tridecyl-2,6-dimethyl morpholine;
4-N-dodecyl-2,6-dimethyl morpholine;

Typical fumigants, growth regulators, repellants, and rodenticides include (See *Agricultural Chemicals*, Book III, *Fumigants*, 1988–1989 Revision, W. T. Thomson, Thomson Publications, Fresno, Calif. 93791):
Growth Regulants:
1,2 Dihydro-6-ethyoxy-2,2,4-trimethylguinoline;
(2-chloroethyl) phosphoric acid;
4-[acetamino methyl]-2-chloro-N-(2,6-diethyl phenyl acetamide;
Benzoic acid, 3,6 dichloro-2-methoxy,2-ethoxy-1-methyl-2-oxo ethyl ester;
Repellants:
O,O-dimethyl-O-[(4-methyl thio)-m-tolyl] phosphorothioate;
Tertiary butyl-sulfenyl dimethyl dithio carbamate;
Seed Softener:
2-chloro-6-(trichloromethyl) pyridine;
5-ethoxy-3-trichloromethyl-1,2,4-thiadiazole;
N-phenyl-N'-1,2,3-thiadiazol-5-yl urea;

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:
Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: O,O-diethyl-O-2,5-dichloro-4-bromophenyl thionophosphate,
N-(2-mercaptoethyl) benzene-sulfenamide (BETASAN®),
Isobornyl Thiocyanoacetate (Thanite®),
Ioxynil ester of octanoic acid,
Molinate S-ethyl hexahydro-1H-azepine-1-carbothioate,
PP 511 O,O-dimethyl-(2-diethylamine 4-methyl-6-pyrimidinyl) carbamate,
PP 211 O,O-diethyl O-(2-diethylamine-4-methyl-6-pyrimidinyl) phosphorocarbamate,
Chlordane,
5-Ethoxy-3-(trichloromethyl)-1,2,4-thiadiazole (TERRAZALE®),
Ethyl-s-s-dipropyl-phosphodithioate (MOCAP®),
S-Ethyl dipropylthiocarbamate (EPTAM®),
S-Ethyl diisobutylthiocarbamate (SUTAN®),
S-n. propyl-di-n-propylthiocarbamate (VERNAM®),
S-propyl butylethylthiocarbamate (TILLAM®),
5-ethyl ethylcyclohexylthiocarbamate (RO-NEET®),
Malathion (S-(1,2-dicarboxyethyl)-O,O-dimethyl phosphorodithioate),
Diazinon (O,O-diethyl,O-(2-isopropyl-4-methyl-6-pyrimidinyl) phosphorothioate, O-Ethyl-S-phenyl-ethylphosphonodithioate (DYFONATE®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dlchlorophenyl)-1-methoxy-1 methyl urea
Atrazine (2-chloro-4-ethylamino-6 isopropylamino-s-triazine)
Simazine (2-chloro-4,6,-bis (ethylamino)-s-triazine
Dodine (n-dodecylguanidine acetate)
Thiram (tetramethylthiuram disulfide)
N-(mercaptomethyl)phthalimide s-(o,o dimethylphosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl) dimethylphosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylaniline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methylpyrimidine*

*Manufacturd by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclopentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl-N-methylurea
NIA 11092 1,1-dimethyl-3-[3-(n-t-butyl carbamyloxy) phenyl] urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlorophenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dlchlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethyl acetamide
CP 31675 2-chloro-N-(2 methyl-6-t-butylphenyl)acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methyl urea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzene
1-(butile carbamoyl)-2-benzimidazol carbamic acid, methyl ester (BENLATE®)

It is to be understood that mixtures of the above agrichemicals can be used to reinforce function or to serve multiple functions, e.g. as an insect repellent and plant growth regulant or any other combination of functions.

The present emulsifiable agriculturally active concentrate is prepared by mixing agchemical, agchemical solubilizer and surfactant at ambient conditions to provide a composition having a Brookfield viscosity of between about 1 and about 1,000 cps; more often, between about 10 and about 500 cps and most usually, 50–200 cps.

The emulsion stabilizer composition and the agrichemical concentrate composition are then combined and mixed for a period of from about 30 minutes to about 4 hours, preferably from about 1 to about 2 hours, until a uniform, single phase emulsion concentrate is obtained, preferably a microemulsion obtained by using large amounts of certain surfactants.

Generally, between about 0.1 and about 20 wt. %, preferably between about 0.5 and about 5 wt. % of the stabilizer solution is mixed with the emulsifiable agchemical concentrate composition to provide a sprayable emulsion concentrate having film forming properties which resists crystallization and breaking of the emulsion upon dilution with water.

In addition to the above defined components, the stabilized concentrate may optionally contain up to 5 wt. % of inert excipients to meet the requirements of a particular formulator. Such inert additives include any of the commercially known flow enhancers, wetting agents, buffers, lubricants, fillers, insect attracting odor agents, fragrance, agrichemical activator etc. For more economical storage and shipment prior to use, the present concentrate can be dried to free-flowing particulate form by adsorption on suitable carriers such as clay, starch, corn cob etc. under mild conditions, e.g. at a temperature of from about 0° C. up to about 30° C.

As stated above, the present polymer solution imparts stability and uniformity as well as film forming properties to the water insoluble concentrate which may be employed as an emulsion, suspension or dispersion. The importance of these functions will be recognized in the handling of the concentrate which is stored until it is transported to the user or is stored by the user before dilution and application to a plant or plant site. In the absence of instant stabilizer, water dilution of the concentrate causes the micelles to coalesce and aglomerate into a gel-like mass. The stabilizing polymer forms a coating on the micelle which prevents coalescence and substantially delays crystal formation and separation from solution, as in steric stabilization. Accordingly, the polymers of the present stabilizing solution are film-forming polymers which not only inhibits coalescence, but also retains the agchemical on the treated site for an extended period. The later function provides an economical benefit in that lower dosages of the active chemical need be applied to achieve comparable results.

Having generally described the invention, reference is now had to the accompanying examples which set forth preferred embodiments but which are not to be construed as limiting to the scope of the invention as more broadly defined above and in the appended claims.

EXAMPLE 1

Formation of a Stable Insecticidal Stable Microemulsion

A pyrethroid concentrate of 2.2 g. TETRAMETHRIN, 16 g. piperonyl butoxide activator, 48.8 g. of N-methylpyrrolidone solvent and 44 g. of a surfactant derived from the mixture of 5 g. N-octylpyrrolidone, 5 g. of $(EO)_2 (PO)_{14} (EO)_2$ block polymer* and 34 g. of Igepal® CO 630** is prepared by mixing the components at room temperature for 1 hour.
*EO is ethylene oxide; PO is propylene oxide
**9 ethoxylated nonyl phenol A stabilizing solution of 20 g. of 80:20 N-vinylpyrrolidone/eicosyl α-olefin copolymer having a No. Av. MW of about 10,000 and 80 g. of butanol is prepared by mixing the copolymer and solvent at ambient temperature and pressure for 1 hour.

Under vigorous mixing and ambient conditions, 5 g. of the stabilizing solution is gradually introduced into 100 g. of concentrate composition and after 2.5 hours a stabilized uniformly distributed, emulsifiable concentrate is obtained. The stabilized concentrate, was then diluted with 900 g. of water and stirred for 2 hours at room temperature, forms a sprayable liquid, single phase microemulsion which retains uniform distribution of the TETRAMETHRIN as liquid droplets for a period of 48 hours without indication of crystal precipitation.

The same concentrate, absent the addition of the stabilizing solution, precipitates TETRAMETHRIN crystals within 24 hours after dilution.

It is also noted that when the stabilized emulsion is applied to a substrate, the copolymer exerts a film forming effect thereon which serves to retain the microemulsion on the plant for an extended period, thus providing the use of smaller dosages of the agrichemical and less frequent application of the chemically active material to provide an equivalent chemical affect.

The same beneficial stabilization is observed when D-ALLETHRIN or PERMETHRIN insecticides are substituted for TETRAMETHRIN in the above example. Also, copolymers having a No. Av. MW of from about 1,000 to about 50,000 can be substituted in this example to provide stabilization of the water diluted microemulsion.

Generally, the polymers suitably employed in the stabilizing solution have a molecular weight (Number Average MW) of from about 500 to about 20,000, preferably from about 800 to about 15,000.

EXAMPLE 2 (Comparative)

Preparation of a Insecticidal Microemulsion

A pyrethroid concentrate (100 g.) leaving the following composition

| Component | Grams |
|---|---|
| Deltamethrin | 8 |
| N-methylpyrrolidone | 10 |
| N-octylpyrrolidone | 10.25 |
| Pegol L31* block polymer | 10.25 |
| Igepal® CO 630 | 61.50 |

*ethylene oxide-propylene oxide-ethyleneoxide block copolymer is mixed in a glass beaker at room temperature for 1 hour whereupon a homogeneous emulsion is obtained.

The concentrate is divided into three equal portions or samples (A, B and C) and each portion separately diluted with deionized water in the following concentrations

| Sample | Parts of $H_2O$/part of Sample |
|---|---|
| A | 100 |
| B | 200 |
| C | 800 |

Upon standing for 48 hours, the solution becomes cloudy and small rod-like crystals separate from solution as seen through a microscope at 200 magnification.

EXAMPLE 3

Example 2 is repeated, except that before dilution of Samples A, B, and C with deionized water, 4 g. of the present stabilizing mixture is added.

The stabilizing solution of this example is prepared by mixing 50 g. of N-vinylpyrrolidone/1-hexadecene (50:50) copolymer having a number average molecular weight of about 5,000 with 50 g. of N-octylpyrrolidone for 24 hours at room temperature. The resulting stabilizing solution (4 g.) is then added to the undiluted concentrate and vigorously mixed for 1 hour at ambient temperature after which a single phase, uniform, microemulsion concentrate is obtained.

The resulting concentrate is then divided into 3 equal portions and each portion or sample diluted with deionized water as described in Example 2. The samples, observed for 120 hours, show no crystal formation as viewed through a microscope at 200 magnification. The solutions, stabilized with the present mixture are sprayable liquids with film-forming properties.

Similar results are obtained when the stabilized emulsion of this example is diluted with hard water containing $MgSO_4$ and $CaCl_2$ expressed as 500 and 1,000 ppm calcium carbonate equivalent.

It is also found that storage of the stabilized, diluted emulsion at 1° C. and at 25° C. has no effect on the absence of crystal formation during at least 120 hours.

EXAMPLE 4 (Comparative)

Preparation of a Miticide Microemulsion

In a glass beaker, 16 g. of pyranica [N-(4-tert-butylbenzyl)4-chloro-3-ethyl-1-methyl-5-pyrazole carboxamide] is dissolved in 16 g. of N-methylpyrrolidone at room temperature. To this solution is added a surfactant mixture of 6 g. N-octylpyrrolidone, 6 g. Pegol L-31 and 36 g. Igepal CO-630. The resulting composition is mixed with 20 g. of water which produced an emulsion concentrate. This concentrate is divided into 6 equal samples. Upon dilution of these sample concentrates with deionized water, a cloudy solution was obtained. The results after dilution are reported in following Table I.

TABLE I

| Samples of Concentrate | Dilution pts. Concentrate/ pts. H₂O | Observation 0 hr. | 16 hr. |
|---|---|---|---|
| 1 | 5/5 | clear but some crystals | gel-long crystals of 400 μ |
| 2 | 2/8 | cloudy | gel-crystals 800 μ |
| 3 | 1/9 | cloudy | cloudy + crystals |
| 4 | 0.5/9.5 | cloudy | cloudy crystals |
| 5 | 0.2/9.8 | cloudy | cloudy crystals |
| 6 | 0.1/9.9 | cloudy | cloudy crystals |

The above procedure was repeated except that 6 g. of a 30% solution of N-vinylpyrrolidone/1-hexadecene copolymer (20:80) having a number average molecular weight of about 5,000 is prepared by dissolving 3 g. of the copolymer in 7 g. of N-octylpyrrolidone and mixing for a period of 4 hours at room temperature and then added to the above formulation before dilution with water. Observation at 16 hours showed the resulting composition remained clear without any crystal formation.

EXAMPLE 5

The following compositions were prepared.

| | grams | |
|---|---|---|
| | Sample 1 | Sample 2 |
| A. Concentrate components | | |
| pyranica | 16 | 16 |
| N-methylpyrrolidone | 16 | 16 |
| N-octylpyrrolidone | 5 | 4 |
| Pegol L-31 | 6 | 6 |
| Igepal CO-630 | 36 | 36 |
| Water | 20 | 20 |
| B. Stabilizer Solution of Example 3 added to concentrate A with vigorous mixing at RT | 0 | 4 |

The resulting stabilized concentrate samples were then diluted and mixed with deionized water as indicated in Table II where the results are reported.

TABLE II

| | pts H₂O/pts Concentrate | Time (hours) 0 | 24 | 48 |
|---|---|---|---|---|
| Sample 5-1 | 5/5 | liquid, crystals present | liquid, crystals present | gel, crystals present |
| | 8/2 | cloudy | gel, crystals 800 μ | gel, crystals 800 μ |
| | 9/1 | cloudy | cloudy, crystals present | cloudy, crystals present |
| | 9.5/0.5 | cloudy | cloudy | cloudy |
| | 9.9/0.1 | cloudy | cloudy | beginning to gel |
| Sample 5-2 | 5/5 | ← liquid no crystals present → | | |
| | 8/2 | ← liquid no crystals present → | | |
| | 9/1 | ← liquid no crystale present → | | |
| | 9.5/0.5 | ← liquid no crystals present → | | |
| | 9.9/0.1 | ← liquid no crystals present → | | |

EXAMPLE 6

The following pesticidal concentrate is prepared by mixing the ingredients at room temperature.

| Pesticide Components | Concentration grams (g.) |
|---|---|
| Diuron[1] | 15 |
| Solvent Mixture | |
| N-octylpyrrolidone | 40 |
| N-methylpyrrolidone | 20 |
| Aromatic petroleum oil (Exxon 220) | 10 |
| Surfactant mixture | |
| GAFAC ® DM 710[2] | 15 |

The resulting concentrate (96 g.) is stabilized with 4 g. of the stabilizer described in Example 3. The stabilized concentrate when diluted with (a) 50 parts deionized water/part concentrate and with (b) 50 parts of hard H₂O/part of concentrate produces a sprayable, film forming emulsion with no crystalization during 2 hour periods of observation. Omission of the stabilizer solution results in noticeable crystalization within the same period.

(1) (N,N-dimethyl-N'-2,4-dichlorophenyl) urea
(2) α-phosphono- and α,α-phosphinico bis-w-(phenoxy) poly(oxy-1,2-ethanediyl)

EXAMPLE 7

Stabilization of a Non-Aqueous Concentrate

A concentrate of 16 g. pyranica dissolved in 20.5 g. N-methylpyrrolidone is combined with a surfactant mixture of 5.7 g. N-octylpyrrolidone, 7.7 g. Pegol L-31 and 46.1 g. Igepal® CO 630. This concentrate (96 g.) is stabilized by the addition of 4 g. of the solution described in Example 3.

Upon dilution of the above concentrate with water at 4 parts water and at 3,000 parts water/part of concentrate, clear emulsions with no crystallization are obtained during the time observed (2 hours).

The diluted concentrate, after storage for 48 hours, shows no sign of gelling.

EXAMPLE 8

A 27% solution of ASSERT bisulfate* in a mixture of N-methylpyrrolidone and GAFAC® 710**, when stored at −2° C. for 48 hours, produced a product containing hard crystals of the solvated bisulfate from the formulation upon seeding with pure crystals, thus indicating the instability of the formulation. However, when 6 g. of 3 parts methyl vinyl ether/maleic acid ester (50:50), dissolved in 7 parts of propylene glycol was added to 94 parts of the above formulation, a stabilized concentrate, substantially free of crystals from solution, even after seeding, was obtained.

*The bisulfate salt of 2-[4,5-dihydro-4-methyl-4-(1-methylethyl)-5-oxo-1H-imidazol-2-yl]methyl benzoate.
** α- and α,α-phosphono-w-(phenoxy)-poly(oxy-1,2-ethanediyl).

What is claimed is:

1. A stabilized agricultural chemical concentrate of
   (a) between about 0.1 and about 20 wt. % of a stabilizer composition comprising (1) between about 10 and about 90 wt. % of a water insoluble, non-crosslinked polymer which is an N-vinyl $C_4$ to $C_7$ lactam/$C_4$ to $C_{20}$ alpha olefin copolymer in a weight ratio of from about 90:10 to about 20:80, wherein said lactam moiety of said lactam polymers are optionally substituted on a ring carbon atom with $C_1$ to $C_4$ alkyl; said polymers of (1) being dissolved in (2) between about 90 and about 10 wt. % of a solvent selected from the group consisting of a N—$C_8$ to $C_{16}$ alkylpyrrolidone, a dibasic acid $C_1$ to $C_4$ alkyl ester, a non-volatile ether having a boiling point above 150° C., an aromatic petroleum distillate fraction boiling between 140°–250° C. and mixtures thereof and
   (b) between about 80 and about 99.9 wt. % of an agrichemical concentrate containing an effective agriculturally active amount of a water insoluble active agrichemical dissolved in between about 10 and about 80 wt. % of an organic solvent and between about 1 and about 30 wt. % of a surfactant mixture having a hydrophilic-lipophilic balance of from 3 to 20, said surfactant being selected from the group consisting of anionic surfactants and non-ionic surfactants and mixtures thereof.

2. The stabilized concentrate of claim 1 wherein the polymer of (a) is a N-vinylpyrrolidone copolymer having a number average molecular weight of from about 1,000 to about 50,000.

3. The stabilized concentrate of claim 1 wherein the polymer of (a) is a copolymer of N-vinylpyrrolidone and a $C_{10}$ to $C_{18}$ alpha-olefin in a weight ratio of from about 30:70 to 70:30.

4. The stabilized concentrate of claim 3 wherein said polymer is the copolymer of N-vinylpyrrolidone and 1-hexadecene in a 50:50 weight ratio.

5. The stabilized concentrate of claim 1 wherein between about 20 and about 70 wt. % of the polymer of (a) is dissolved in a N—$C_8$ to $C_{12}$ alkylpyrrolidone.

6. The stabilized concentrate of claim 5 wherein the polymer solvent is N-octylpyrrolidone.

7. The stabilized concentrate of claim 1 wherein between about 0.5 and about 5 wt. % of (a) is present in the composition.

8. The stabilized concentrate of claim 1 wherein said agrichemical concentrate has a Brookfield viscosity of from about 1 to about 1,000 cps and contains between about 5 and about 50 wt. % of an active agrichemical, between about 10 and about 80 wt. % solvent, between about 1 and about 30 wt. % of a non-ionic/anionic surfactant mixture or a non-ionic surfactant mixture to provide a hydrophilic-lipophilic balance of from 7 to 15 and between about 0 and about 30 wt. % water.

9. The stabilized concentrate of claim 8 wherein said agrichemical concentrate has a Brookfield viscosity of from about 10 to about 500 cps and contains between about 15 and about 25 wt. % of the agrichemical.

10. The stabilized concentrate of claim 8 wherein said surfactant mixture has a hydrophilic-lipophilic balance of from about 8 to about 12.

11. The stabilized concentrate of claim 1 which is diluted to at least 85 wt. % water.

12. The diluted, stabilized concentrate of claim 11 which is diluted with from about 90 to about 99.5 wt. % water.

13. The diluted, stabilized concentrate of claim 11 which contains between about 0.5 and about 5 wt. % of (a) and between about 2 ppm and about 2 wt. % of said agrichemical.

14. The stabilized concentrate of claim 1 which is dried to a free-flowing particulate solid.

* * * * *